United States Patent [19]

Dorschner et al.

[11] 4,069,036

[45] Jan. 17, 1978

[54] N-HALOACYL 4-SPIROCYCLOALIPHATIC OXAZOLIDINES

[75] Inventors: Kenneth P. Dorschner, Vienna, Va.; James A. Albright, St. Louis, Mich.

[73] Assignee: SCM Corporation, New York, N.Y.

[21] Appl. No.: 534,824

[22] Filed: Dec. 20, 1974

Related U.S. Application Data

[63] Continuation-in-part of Ser. No. 280,836, Aug. 15, 1972, Pat. No. 3,859,292.

[51] Int. Cl.² .................... C07D 263/04; A01N 9/22
[52] U.S. Cl. .................................. 71/88; 260/307 FA
[58] Field of Search ...................... 260/307 FA; 71/88

[56] References Cited

U.S. PATENT DOCUMENTS

| | | | |
|---|---|---|---|
| 3,707,541 | 12/1972 | Lajiness | 260/244 R |
| 3,825,555 | 7/1974 | Lajiness | 260/307 F |
| 3,881,908 | 5/1975 | Dorschner et al. | 71/88 |
| 3,884,671 | 5/1975 | Albright et al. | 71/88 |

FOREIGN PATENT DOCUMENTS

| | | | |
|---|---|---|---|
| 2,341,810 | 2/1974 | Germany | 260/307 A |
| 124,228 | 11/1974 | Japan | 260/307 A |

OTHER PUBLICATIONS

Albright et al., Chem. Abst. vol. 80: 1461/40 u (1974).

*Primary Examiner*—Donald G. Daus
*Assistant Examiner*—Mary C. Vaughn
*Attorney, Agent, or Firm*—A. Joseph Gibbons

[57] ABSTRACT

Certain N-($C_{2-4}$ haloalkanoyl) oxazolidines having the 4-carbon atom valences satisfied by certain alkylene groups, thus forming with the respective ring-carbon a spirocycloaliphatic group containing from 5 to 12 carbon atoms, are selective herbicides for crop protection.

22 Claims, No Drawings

N-HALOACYL 4-SPIROCYCLOALIPHATIC OXAZOLIDINES

RELATED ART

This application is a continuation-in-part application based on pending application Ser. No. 280,836, filed Aug. 15, 1972, now U.S. Pat. No. 3,859,292, which is incorporated by reference herein. Also incorporated herein by reference is the copending application Ser. No. 280,851, now abandoned, filed concurrently with Ser. No. 280,836 on Aug. 15, 1972.

BACKGROUND OF THE INVENTION

This invention relates to substituted oxazolidines and more particularly to N-haloacyl (2-alkylated) oxazolidines, herbicidal compositions containing same, and a process for controlling plant growth with same. The closest art known to applicants are the copending applications by the same inventors, namely, Ser. Nos. 280,851 and 280,836 filed on Aug. 15, 1972 and their respective divisional cases Ser. Nos. 383,348 now U.S. Pat. No. 3,881,908, and 383,349 now U.S. Pat. No. 3,884,671.

The oxazolidine ring is a 5-member carbocyclic ring having an oxygen atom at the one position and a nitrogen atom at the three position, thus:

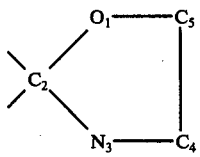

Various derivatives heretofore have been suggested for use as herbicides, insecticides, microbiocides, microbiostats, and pharmaceuticals.

SUMMARY OF THE INVENTION

One aspect of this invention is an N-haloacyl (2-alkylated) oxazolidine wherein the haloacyl group is $C_{2-4}$ acyl and the 4 and 5 carbon atoms valences of the oxazolidine ring are satisfied by hydrogen atoms or $C_{1-6}$ alkyl groups.

A second aspect of this invention is an oxazolidine selected from the group consisting of (4-spirocycloaliphatic) and (5-spirocyloaliphatic) N-haloacyl oxazolidine, wherein the haloacyl group contains 2 to 4 carbon atoms, the 2-carbon atom valences are satisfied with at least one $C_{1-6}$ alkyl group, the remaining ring-carbon atom valences are satisfied by hydrogen or $C_{1-6}$ alkyl groups and said spirocycloaliphtic group contains 5 to 12 carbon atoms being selected from the group consisting of cyclopentyl, cyclohexyl, cyclohexenyl, cycloheptyl, cyclooctyl and $C_{1-3}$ lower alkyl substituted derivatives thereof.

Another aspect of this invention is a herbicidal composition comprising about 1-98% of such oxazolidine and an agriculturally acceptable carrier therefor.

Still another aspect of this invention is a process for controlling growth of vegetation which comprises applying to the locus of such vegetation such oxazolidine at the rate of about 0.5-15 pounds per acre.

DETAILED DESCRIPTION OF THE INVENTION

The subject compounds can be depicted structurally as follows:

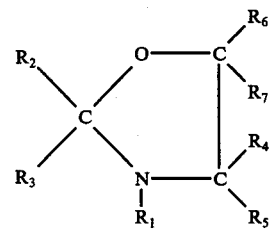

$R_1$ is a $C_{2-4}$ haloacyl group, e.g., chloroacetyl;
$R_2$ and $R_3$ are independently a $C_{1-12}$ alkyl group or hydrogen; $R_4$, $R_5$, $R_6$, and $R_7$ are individually hydrogen atoms or lower ($C_{1-6}$) alkyl groups; when $R_4$ and $R_5$ or $R_6$ and $R_7$ are taken together they represent an alkylene or a lower-alkyl substituted alkylene thus forming a spirocycloaliphatic ring with the 4 or 5 ring carbon atom.

The haloacyl group of oxazolidine nitrogen atom is of special importance for achieving herbicidal effectiveness. For efficiency and economy the advantageous haloacyl groups are chlorinated, preferably monochlorinated, but multiple halogenation can be practiced. The halogen of said haloacyl group also can be bromine, iodine and/or fluorine. Additionally, such haloacyl group advantageously is haloacetyl for efficiency and economy, but halopropionyl and halobutyryl radicals (normal and isomeric) also can be used.

In general, for efficiency and economy of preparation and general herbicidal use the alkylation on the 2-carbon atom of the oxazolidine ring advantageously is at least one $C_{1-12}$ straight or branched chain alkyl group, frequently two alkyl groups (in such instances often unsymmetrical alkylation), and especially lower ($C_{1-6}$) alkylation. It is, of course, within the skill of the art to replace at least such higher molecular weight alky radicals with alkenyl radicals, or even the propyl radical with an allyl radical, or to replace hydrogen atoms on any such hydrocarbyl group with halogen, carbontrile, nitro, alkoxy, mercapto, amido, ester, thioester, and hydroxy groups.

Oxazolidine derivatives wherein the substituent groups at the 4 and/or 5 ring position taken together represent an alkylene group provide particularly effective herbicides and are represented by the formula:

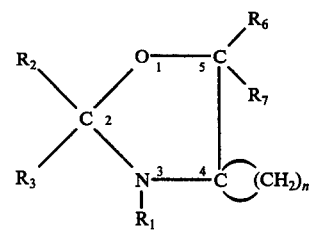

Compounds wherein $n$ is 5 and where $R_2$ and $R_3$ are lower alkyl are especially preferred because of their ease of preparation and their herbicidal selectivity. Spirocycloaliphatic substitution at the 4-ring position are preferred because of their herebicidal effectiveness and ease of preparation. In general, we have found that the most herbicidally effective of the instant compounds are those having alkylation on the 4 or 5 carbon atoms of the oxazolidine ring, particularly those having plural alkylation and cycloalkylation at the 4 carbon atom.

Application dosages of these herbicides, based on the active ingredient, suitably can be fairly high, but for economy generally are about 15 pounds per acre or below, advantageously not more than about 8 pounds per acre, and generally 0.5-8 pounds per acre, although dosages as high as 40 pounds per acre can be used.

By crop plants is meant not only agricultural crops which are used for food supply of man and animals, but also includes other plants such as lawn grass species where broad leaf and other undesirable weeds are to be controlled, supressed, or eradicated. In general, oxazolidines of this invention are effective in the elimination or control of weeds including coffeeweed (Sesbania, spp.), pigweed (Amaranthus, spp.), crabgrass (Digitario, spp.), barnyard grass (Echinochloa, spp.), without significant injury to the specific crops such as corn, cotton, peanuts, and soybeans.

The compounds of the present invention are, in general, herbicidal in both pre- and post-emergent applications. For pre-emergent control of undesirable vegetation, the herbicidal compounds will be applied in herbicidally effective amounts to the locus or growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foliage and other plant parts. Generally, the herbicidal compounds of the invention are effectively against weed grasses as well as broadleaved weeds. Some may be selective with respect to the type of application and/or type of weed.

Although compounds of the present invention can be used alone as herbicides, it is generally desirable to apply the compounds in herbicidal compositions comprising one or more of the herbicidal compounds intimately admixed with a biologically inert carrier. The carrier may be a liquid diluent or a solid, e.g., in the form of dust powder or granules. In the herbicidal composition, the active herbicidal compounds can be from about 0.01 to 95% by weight of the entire composition.

Suitable liquid diluent carriers include water and organic solvents, e.g., hydrocarbons such as benzene, toluene, kerosene, diesel oil, fuel oil, and petroleum naphtha. Suitable solid carriers are natural clays such as kaolinite, atapulgite, and montmorillonite. In addition, talcs, pyrophillite, diatomaceous silica, synthetic fine silicas, calcium aluminosilicate and tricalcium phosphate are suitable carriers. Organic materials such as walnutshell flour, cottonseed hulls, wheat flour, wood flour or redwood-bark flour may also be used as solid carriers.

The herbicidal composition will also usually contain a minor amount of a surface-active agent. Such surface agents are those commonly known as wetting agents, dispersing agents and emulsifying agents and can be anionic, cationic or nonionic in character. The herbicidal compositions may also contain other pesticides, adjuvants, stabilizers, conditioners, fillers, and the like.

The amount of herbicidal compound or composition administered will vary with the particular plant part or plant growth medium which is to be contacted, the general location of application—i.e., sheltered areas such as greenhouses, as compared to exposed areas such as fields—as well as the desired type of control. Generally for both pre- and post-emergent control, the herbicidal compounds of the invention are applied at rates of 0.2 to 60 kg/ha, and the preferred rate is in the range 0.5 to 40 kg/ha.

The characteristic of a good selective herbicide is that when it is applied near or on the foliage of the crop plant, only the weed species is killed while the valuable crop plants are not harmed beyond the point of recovery, thus allowing a high percentage (85–100 percent) to mature to harvestable crops. We have found the following compounds representative of the types most efficacious as selective herbicides:

3-($\alpha$-chloroacetyl)-2,2-dimethyl-4-cyclohexanespiro oxazlidine 3-($\beta$-bromopropionyl(-2,2-diethyl-4-cyclohexanespiro oxazolidine 3-($\gamma$-fluoropropionyl)-2,2-dimethyl-4-cyclohexanespiro oxazolidine 3-($\alpha$-chloroacetyl)-2,2-dimethyl-4-cycloheptanespiro oxazolidine.

3-($\alpha$-chloroacetyl)-2,2,5-trimethyl-4-cyclohexanespiro oxazolidine 3-($\alpha$-chloroacetyl)-2,2-dimethyl-5-cyclohexanespiro oxazolidine 3-($\alpha$-chloroacetyl)-2,2,4-trimethyl-5-cyclohexanespiro oxazolidine.

3-($\alpha$-chloropropionyl)2-methyl-2-propyl-4(3'-methylcyclohexane) spiro oxazolidine 3-($\beta$-chloropropionyl)-2,2-dipropyl-4(4'-methylcyclohexane) spiro oxazolidine 3-($\alpha$-chloroacetyl)-4-cyclohexanespiro oxazolidine 3-($\alpha$-chloroacetyl)-2-methyl-4-cyclohexanespiro oxazolidine

SYNTHESIS

The unacylated oxazolidine intermediates for preparing the subject compounds can be synthesized conveniently by reacting substituted amino alkanols with ketones. A substantial list of these compounds is given in the review article "The Oxazolidines," E. D. Bergman, Chem. Rev., 53, 309 (1953). Usually, the amino alcohol and the ketone are heated together in an inert hydrocarbon solvent, and by-product water is separated from the condensed azeotropic mixture of hydrocarbon and water in a Dean-Stark water separator. The solvent is then evaporated and the product purified by distillation under reduced pressure. Suitable reaction solvents are water immiscible hydrocarbons such as benzene, toluene and the like. Benzene is a preferred solvent because of its low boiling point.

The N-haloacyl oxazolidines of this invention can be synthesized by reacting the corresponding intermediate oxazolidine with the desired haloalkylcarbonyl chloride (also described as a haloacyl chloride) at a temperature in the range of about 50° C. to about 250° C. in the presence of an acid-acceptor. The reaction is preferably carried out in an organic solvent, inert under the conditions of the reaction as for example, acetonitrile, benzene, xylene and the like; hydrocarbon solvents are generally preferred. The acid-acceptor is generally a basic substance which forms water soluble by-products, easily separable from the main reaction product. Although the acid-acceptor can sometimes be alkali metal salts of weak acids, such as sodium or potassium carbonate, or acetate, it is preferable to use a tertiary amine. Useful and common tertiary amines are, for example, triethylamine and pyridine; frequently the crystalline hydrohalide formed as a by-product is insoluble in the reaction solvent and easily removed by filtration. When a hydrocarbon solvent is used the product is soluble in the reaction solvent and workup is conveniently carried out by filtering the by-product amine hydrohalide, washing the remaining organic phase with water, and removing the reaction solvent by evaporation or distillation. Thereafter, the product can usualy be purified by conventional distillation procedures including ones at subatmospheric pressure.

The following examples are intended to illustrate the invention but not to limit the scope thereof, parts and percentages being by weight unless otherwise indicated.

EXAMPLE 1

3-(α-chloroacetyl)-2,2-dimethyl-4-cyclohexanespiro oxazolidine

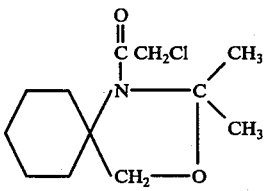

A solution of 10 g. (0.078 mol) 1-(hydroxymethyl) cyclohexyl amine [M. S. Newman and W. M. Edwards J. Amer. Chem. Soc. 76 1840 (1954)] and 5 g. (0.12 mol) acetone in 100 ml benzene was heated under reflux for 7 hours in a flask equipped with a Dean-Stark trap. A total of 3.2 ml of water was separated and removed from the reaction mixture with the trap. The benzene and excess acetone were then evaporated under reduced pressure to give 11.5 g. of 2,2-dimethyl-4-cyclohexanespiro oxazolidine, as a pale yellow oil. The NMR spectrum of the product showed a sharp single for the 2,2-dimethyl groups at 1.4δ (relative to tetramethylsilane).

A 3.7 g. (0.033 mol) sample of chloroacetyl chloride was added dropwise to an ice bath-cooled solution of 5 g. (0.03 mol) 2,2-dimethyl-4-cyclohexanespiro oxazolidine, prepared as described above; and 3.3 g. (0.033 mol) of triethylamine in 25 ml. methylene chloride. After the addition was completed, the ice bath was removed and the reaction mixture was stirred at ambient temperature for a half hour. The reaction mixture was then washed with 20 ml. water, dried over magnesium sulfate and evaporated under reduced pressure to give a dark brown oil. The oil was chromatographed on silica gel (hexane/benzene/methylene chloride eluants) to give the N-acetylated product (RE 19,970) as a white solid (2.8 g.) which melted at 81°–83° C after recrystallization from hexane/benzene. Elemental analysis for $C_{12}H_{20}ClNO_2$ showed: % Cl, calc, 14.4, found 13.3.

EXAMPLE 2

3-(α-chloroacetyl)-2-methyl-2-propyl-4-cyclohexanespiro oxazolidine

A solution of 11 g. (0.085 mol) 1-(hydroxymethyl) cyclohexyl amine and 8.1 g. (0.94 mol) 2-pentanone in 150 ml benzene was heated under reflux in a flask equipped with a Dean-Stark trap for water removal. After refluxing for a total of 19 hours, NMR analysis of the reaction showed that only a trace amount of 1-(hydroxymethyl) cyclohexyl amine remained in the reaction mixture. The reaction mixture was then evaporated under reduced pressure to give the crude 2-methyl-2-propyl-4-cyclohexanespiro oxazolidine product, as an oil.

A 5.4 g. (0.047 mol) sampe of chloroacetyl chloride was added dropwise to an ice bath-cooled solution of 8.5 g. (0.043 mol) 2-methyl-2-propyl-4-cyclohexanespiro oxazolidine, prepared as described above, and 4.8 g. (0.047 mol) triethylamine in 50 ml. methylene chloride. After the addition was completed, the ice bath was removed and the reaction mixture stirred at ambient temperature for 2½ hours. The reaction mixture was then washed with 25 ml. water, dried over magnesium sulfate, and evaporated under reduced pressure to give a dark brown oil. The oil was chromatographed on silica gel (benzene eluant) to give the N-acetylated product as a brown oil. Elemental analysis for $C_{14}H_{24}ClNO_2$ showed: % Cl, calc. 13.0, found 13.9.

EXAMPLE 3

Evaluation as Pre-emergence Herbicide

An acetone solution of the test compound was prepared by mixing 750 mg. of the compound, 220 mg. of a nonionic surfactant and 25 ml. of acetone. This solution was added to approximately 125 ml. of water combining 156 mg. of surfactant.

Seeds of the test vegetation were planted in a pot of soil and the test solution was sprayed uniformly onto the soil surface at a dose of 33 mcg/cm$^2$. The pot was watered and placed in a greenhouse. The pot was watered intermittently and was observed for seedling emergence, health of emerging seedlings, etc., for a 3-week period. At the end of this period, the herbicidal effectiveness of the compound was rated based on the physiological observations. A 0 to 100 scale was used, 0 representing no phytotoxicity, 100 representing complete kill.

EXAMPLE 4

The compound of Example 1 was tested as a pre-emergence herbicide using a procedure similar to that of Example 3. The selectivity in protecting sweet corn, wheat, oats, sorghum and rice while effectively controlling Bermuda Grass, Yellow Nutsedge, Johnson Grass, Cheat Grass, Yellow Foxtail and Rye Grass is shown in Table 1.

EXAMPLE 5

The compound of Example 1 was further evaluated as a pre-emergence herbicide using the commercial herbicides Atrazine and Lasso as controls. The selectivity of this compound in protecting pea, cotton, soybean, sugar beets and alfalfa is shown in Table 2.

EXAMPLE 6

Evaluation as Post-emergent Herbicide

The test compound was formulated in the same manner as described above for the pre-emergent test. The concentration of the test compound in this formulation was 5000 ppm. This formulation was uniformly sprayed on 2 similar pots of 24-day old plants (approximately 15 to 25 plants per pot) at a dose of 33 mcg/cm$^2$. After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0 to 100 scale was used, 0 representing no phytotoxicity and 100 representing complete kill. The compound of Example 1 was effective in controlling the growth of Wild Oats, Avena fatua (25) and Watergrass, *Echinochloa crusgalli* (80).

EXAMPLE 7

When the spirocyclohexane group in the compound of Example 1 is replaced by a spirocycloaliphatic group containing 5 to 12 carbon atoms including cyclopentyl, cyclohexenyl, cycloheptyl and the 3- and 4-methyl substituted derivatives thereof such compound will exhibit herbicidal properties essentially equivalent to that of the compound of Example 1.

TABLE 1

PRE-EMERGENCE HERBICIDAL EVAULUATION

| Compound | Conc. Al γ/cm$^2$ | Bermuda Grass | Yellow Nutsedge | Johnson Grass | Cheat Grass | Yellow Foxtail | Rye Grass | m | Sweet Corn | Wheat | Oats | Sorghum | Rice |
|---|---|---|---|---|---|---|---|---|---|---|---|---|---|
| Example 1 | 11 | 95 | 88 | 80 | 28 | 100 | 90 | 80 | 0 | 8 | 7 | 17 | 42 |
|  | 4.4 | 62 | 52 | 30 | 7 | 100 | 48 | 50 | 0 | 7 | 7 | 2 | 12 |
|  | 1.8 | 32 | 37 | 7 | 0 | 100 | 3 | 30 | 0 | 0 | 0 | 0 | 0 |
|  | 0.7 | 27 | 18 | 0 | 0 | 72 | 0 | 20 | 0 | 0 | 0 | 0 | 0 |
| Atrazine* | 11 | 100 | 2 | 7 | 35 | 83 | 100 | 55 | 0 | 99 | 100 | 2 | 97 |
|  | 4.4 | 93 | 3 | 13 | 27 | 40 | 100 | 46 | 0 | 95 | 96 | 0 | 88 |
|  | 1.8 | 77 | 0 | 7 | 3 | 10 | 80 | 30 | 0 | 70 | 88 | 0 | 75 |
|  | 0.7 | 22 | 0 | 3 | 3 | 0 | 20 | 8 | 0 | 20 | 18 | 0 | 8 |
| Lasso* | 11 | 99 | 100 | 100 | 98 | 100 | 100 | 100 | 0 | 32 | 88 | 100 | 97 |
|  | 4.4 | 99 | 100 | 100 | 50 | 100 | 100 | 92 | 0 | 15 | 55 | 75 | 70 |
|  | 1.8 | 100 | 100 | 100 | 28 | 100 | 83 | 85 | 0 | 5 | 30 | 33 | 37 |
|  | 0.7 | 95 | 82 | 93 | 3 | 100 | 63 | 73 | 0 | 0 | 5 | 0 | 12 |

*Controls

TABLE 2

PRE-EMERGENCE HERBICIDE EVALUATION

| Compound | Conc. Al γ/cm | Teaweed | Field Bindweed | Vetch | Plantain | Curly Dock | Dandelion | m | Pea | Cotton | Soybean | Sugar Beets | Alfalfa |
|---|---|---|---|---|---|---|---|---|---|---|---|---|---|
| Example 1 | 11 | 27 | 8 | 60 | 50 | 25 | 73 | 41 | 5 | 0 | 2 | 3 | 7 |
|  | 4.4 | 5 | 5 | 8 | 30 | 10 | 60 | 20 | 0 | 0 | 0 | 0 | 3 |
|  | 1.8 | 3 | 3 | 5 | 8 | 3 | 3 | 4 | 0 | 0 | 0 | 0 | 0 |
|  | 0.7 | 0 | 0 | 0 | 0 | 0 | 0 | 0 | 0 | 0 | 0 | 0 | 0 |
| Atrazine | 11 | 99 | 100 | 85 | 98 | 98 | 99 | 97 | 99 | 97 | 99 | 100 | 100 |
|  | 4.4 | 100 | 100 | 100 | 98 | 98 | 100 | 99 | 40 | 70 | 99 | 100 | 100 |
|  | 1.8 | 100 | 80 | 53 | 99 | 98 | 100 | 88 | 8 | 7 | 100 | 100 | 100 |
|  | 0.7 | 83 | 18 | 27 | 40 | 47 | 99 | 52 | 0 | 0 | 28 | 100 | 99 |
| Lasso | 11 | 47 | 5 | 99 | 100 | 99 | 99 | 75 | 15 | 5 | 3 | 47 | 55 |
|  | 4.4 | 5 | 3 | 38 | 77 | 48 | 83 | 42 | 3 | 2 | 2 | 18 | 22 |
|  | 1.8 | 3 | 10 | 87 | 100 | 53 | 99 | 59 | 2 | 0 | 0 | 2 | 12 |
|  | 0.7 | 0 | 0 | 7 | 1 | 7 | 52 | 13 | 0 | 0 | 0 | 0 | 3 |

What is claimed is:

1. An N-haloalkanoyl 4-spirocycloaliphatic oxazolidine, wherein the haloalkanoyl group has 2 to 4 carbon atoms, the remaining oxazolidine ring-carbon atom valences are satisfied by hydrogen or $C_{1-6}$ alkyl groups, and said spirocycloaliphatic group contains 5 to 12 carbon atoms and is selected from the group consisting of cyclopentyl, cyclohexyl, cyclohexenyl, cycloheptyl, cyclooctyl wherein said cycloaliphatic groups are unsubstituted or substituted with $C_{1-6}$ lower alkyl groups.

2. The oxazolidine of claim 1 wherein halo is chloro.

3. The oxazolidine of claim 1 wherein said 4-spirocycloaliphatic group is cyclohexyl.

4. The oxazolidine of claim 1 wherein said haloalkanoyl group is haloacetyl.

5. 3-(α-chloroacetyl)-2,2-dimethyl-4-cyclohexanespiro oxazolidine.

6. The oxazolidine of claim 1 wherein said haloalkanoyl group is α-chloroacetyl.

7. An N-haloalkanoyl 4-spirocycloaliphatic oxazolidine dialkylated in the 2-position with $C_{1-6}$ alkyl groups wherein the haloalkanoyl group contains 2 to 4 carbon atoms, the remaining oxazolidine ring-carbon atom valences are satisfied by hydrogen or $C_{1-6}$ alkyl groups, and said spirocycloaliphatic group contains 5 to 12 carbon atoms and is selected from the group consisting of cyclopentyl, cyclohexyl, cyclohexenyl, cycloheptyl, cyclooctyl wherein said cycloaliphatic groups are unsubstituted or substituted with $C_{1-6}$ lower alkyl groups.

8. The compound of claim 7 wherein the spirocycloaliphatic group is cyclohexyl.

9. The compound of claim 7 wherein the 2-position alkyl groups are methyl groups and the remaining oxazolidine ring-carbon atom valences are satisfied by hydrogen.

10. The compound of claim 7 wherein the haloalkanoyl group is α-chloroacetyl.

11. A herbicidal composition comprising an agricultural carrier and an herbicidal amount of about 1-98% of an N-haloalkanoyl 4-spirocycloaliphatic oxazolidine, wherein the haloalkanoyl group has 2 to 4 carbon atoms, the remaining ring-carbon atom valences are satisfied with hydrogen atoms or $C_{1-6}$ alkyl groups, and said spirocycloaliphatic group is cyclopentyl, cyclohexyl, cycloheptyl or cyclooctyl.

12. A process for protecting crop plants from undesirable growth of other unwanted vegetation which comprises applying to the locus thereof a herbicidal amount of a 4-spirocycloaliphatic N-haloalkanoyl oxazolidine wherein the haloalkanoyl group has 2 to 4 carbon atoms, the remaining ring-carbon atom valences are satisfied with hydrogen atoms or $C_{1-6}$ alkyl groups, and said spirocycloaliphatic group contains 5 to 12 carbon atoms being selected from the group consisting of cyclopentyl, cyclohexyl, cyclohexenyl, cycloheptyl, cyclooctyl wherein said cycloaliphatic groups are unsubstituted or substituted with $C_{1-6}$ lower alkyl groups.

13. The process of claim 12 wherein the oxazolidine is a 4-cyclohexanespiro oxazolidine.

14. The process of claim 13 wherein the oxazolidine is 3-(α-chloroacetyl)-2,2-dimethyl-4-cyclohexanespiro oxazolidine.

15. A process for protecting crop plants from undesirable growth of vegetation which comprises applying to the locus thereof a herbicidally effective amount of an N-haloalkanoyl 4-spirocycloaliphatic oxazolidine dialkylated in the 2-position with $C_{1-6}$ alkyl groups wherein the haloalkanoyl group contains 2 to 4 carbon atoms, the remaining oxazolidine ring -carbon atom valences are satisfied with hydrogen atoms or $C_{1-6}$ alkyl groups, and said spirocycloaliphatic group contains 5 to 12 carbon atoms and is selected from the group consisting of cyclopentyl, cyclohexyl, cycloheptyl, or cyclooctyl.

16. The process of claim 15 wherein the spirocycloaliphatic group is cyclohexyl.

17. The process of claim 15 wherein the 2-position alkyl groups are methyl groups and the remaining oxazolidine ring-carbon atom valences are satisfied by hydrogen.

18. The process of claim 15 wherein the haloalkanoyl group is α-chloroacetyl.

19. A herbicidal composition comprising an agricultural carrier and an amount in the range from about one percent to about ninety-eight percent by weight of the composition of an N-haloalkanoyl 4-spirocycloaliphatic oxazolidine that is dialkylated in the 2-position with $C_{1-6}$ alkyl groups and wherein the haloalkanyl group contains from 2 to 4 carbon atoms, the remaining oxazolidine ring-carbon atoms are satisfied by hydrogen or $C_{1-6}$ alkyl groups, and said spiroaliphatic group contains 5 to 12 carbon atoms and is selected from the group consisting of cyclopentyl, cyclohexyl, cyclohexenyl, cycloheptyl, cyclooctyl wherein said cycloaliphatic groups are unsubstituted or substituted with $C_{1-6}$ lower alkyl groups.

20. A composition in accordance with claim 19 wherein the spirocycloaliphatic group is cyclohexyl.

21. A composition in accordance with claim 19 wherein the haloalkanoyl group is α-chloroacetyl.

22. A herbicidal composition comprising an agricultural carrier and an amount in the range of from about one percent to about ninety-eight percent by weight of the composition of 3-(α-chloroacetyl)-2,2-dimethyl-4-cyclohexanespiro oxazolidine.

\* \* \* \* \*

UNITED STATES PATENT AND TRADEMARK OFFICE
CERTIFICATE OF CORRECTION

PATENT NO. : 4,069,036
DATED : January 17, 1978
INVENTOR(S) : Kenneth P. Dorschner and James A. Albright It is certified that error appears in the above-identified patent and that said Letters Patent are hereby corrected as shown below:

Col. 1, line 56, change "spirocycloaliphtic" to --spirocycloaliphatic--. Col. 2, line 42, change "alky" to --alkyl--. Col. 3, line 15, change "supress" to --suppressed--; line 33, change "effectively" to --effective--. Col. 4, line 16, change "oxazlidine" to --oxazolidine--; line 17, change "(β-bromopropionyl(" to --(β-bromopropionyl)--. Col. 5, line 9, change "usualy" to --usually--; line 38, change "single" to --singlet--. Col. 6, line 4, change "sampe" to --sample--. Col. 8, line 1, change "contains" to --has--. Col. 9, line 10, change "contains" to --has--. Col. 10, line 6, change "haloalkanyl" to --haloalkaryl--; line 7, change "contains" to --has--.

*Signed and Sealed this*

*Twentieth* Day of *June 1978*

[SEAL]

Attest:

RUTH C. MASON
*Attesting Officer*

DONALD W. BANNER
*Commissioner of Patents and Trademarks*